(12) United States Patent
Oda et al.

(10) Patent No.: US 6,531,626 B1
(45) Date of Patent: Mar. 11, 2003

(54) METHOD FOR PRODUCING CYCLOPROPANECARBOXYLATES

(75) Inventors: Yoshiaki Oda, Toyonaka; Makoto Yako, Takatsuki, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/414,001

(22) Filed: Oct. 7, 1999

(30) Foreign Application Priority Data

Oct. 8, 1998 (JP) .......................................... 10-286525

(51) Int. Cl.⁷ .............................................. C07C 69/74
(52) U.S. Cl. ....................................................... 560/124
(58) Field of Search ........................... 560/124; 562/506

(56) References Cited

U.S. PATENT DOCUMENTS

| | | | |
|---|---|---|---|
| 2,820,023 A | | 1/1958 | Cavanaugh et al. |
| 4,116,998 A | | 9/1978 | Makinson et al. |
| 4,233,232 A | * | 11/1980 | Howarth |
| 4,310,464 A | * | 1/1982 | Costain et al. |
| 4,328,363 A | * | 5/1982 | Heiba et al. |
| 4,333,950 A | * | 6/1982 | Engel |
| 4,429,149 A | * | 1/1984 | Engel |

FOREIGN PATENT DOCUMENTS

| | | | |
|---|---|---|---|
| FR | 1138419 A | | 6/1957 |
| GB | 2005269 | * | 4/1979 |
| JP | 52 128336 A | | 10/1977 |
| JP | 52 128337 A | | 10/1977 |
| JP | 53 130627 A | | 11/1978 |
| JP | 53 147040 A | | 12/1978 |
| JP | 54 59265 A | | 5/1979 |
| JP | 54 81235 A | | 6/1979 |
| JP | 7330671 A | | 12/1995 |
| JP | 9239270 A | | 9/1997 |

OTHER PUBLICATIONS

Okano, Tamon et al. Chem. Lett. (1995), (3), p 246.*
Fu, Xiao–Lin et al., Chinese Journal of Chemisty, vol. 15, No. 1, pp. 90–93, (1997).
Ishii, Yasutaka et al., J. Org. Chem., vol. 61, No. 9, pp. 3088–3090, (1996).
Okano, Tamon et al., Bull. Chem. Soc. Jpn., vol. 66, pp.1863–1865, (1993).
Okano, Tamon et al., Chem. Lett., vol. 3, p. 246, (1995).
The 22nd Symposium on Rare Earth Metal, pp. 44–45, (1993).

* cited by examiner

*Primary Examiner*—Gary Geist
*Assistant Examiner*—Robert W. Deemie
(74) *Attorney, Agent, or Firm*—Birch Stewart Kolasch & Birch LLP

(57) ABSTRACT

There is disclosed a method for producing cyclopropanecarboxylates of the formula (3):

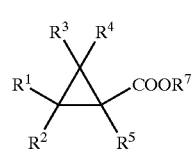

(3)

by transesterification in the presence of a lanthanoid metal alkoxide

12 Claims, No Drawings

METHOD FOR PRODUCING CYCLOPROPANECARBOXYLATES

FIELD OF THE INVENTION

The present invention relates to a method for producing cyclopropanecarboxylates.

DESCRIPTION OF THE RELATED ART

As a method for producing cyclopropanecarboxylic acid ester, there has been disclosed a transesterification method in which cyclopropanecarboxylic acid ester compounds having various alcohol residues have been produced by using sodium alkoxide or Ti alkoxide as a catalyst from a cyclopropanecarboxylic acid ester having a lower alcohol residue and a desired alcohol GB Patent 15581/76, DE Patent 2822472, GB Patent 2005269).

However, said sodium alkoxide catalyst has problems in that it affects stereochemistry such as cis-trans ratio of the resulting ester compounds, and these methods are not always satisfactory for industrial production due to a large amount of by-products formed during the reaction.

SUMMARY OF THE INVENTION

An object of the present invention is to provide a method for producing desired cyclopropanecarboxylic acid esters by transesterification with a corresponding monohydroxy compound in good yield.

The present invention provides:

a method for producing cyclopropanecarboxylate of the formula (3):

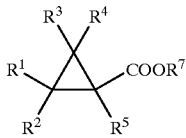

(3)

wherein $R^1$, $R^2$, $R^3$, $R^4$ and $R^5$ each independently represent:
a hydrogen atom, halogen atom,
an optionally substituted alkyl group,
an optionally substituted alkenyl group,
an optionally substituted aralkyl group or
an optionally substituted aryl group; and
$R^7$ represents:
an optionally substituted alkyl group,
an optionally substituted aralkyl group, or
an optionally substituted aryl group,
which comprises:
reacting a cyclopropanecarboxylate of the formula (1)

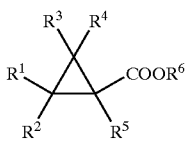

(1)

wherein $R^1$, $R^2$, $R^3$, $R^4$ and $R^5$ are as defined above, and
$R^6$ represents an alkyl group having 1 to 10 carbon atoms or an optionally substituted phenyl group, with a monohydroxy compound of the formula (2):

$$R^7OH \qquad (2)$$

wherein $R^7$ is the same as defined above, in the presence of a lanthanoid metal alkoxide.

DESCRIPTION OF THE PREFERRED EMBODIMENTS

In the present invention at least one lanthanoid metal alkoxide selected from alkoxide compounds of La, Ce, Pr, Nd, Pm, Sm, Eu, Gd, Tb, Dy, Ho, Er, Tm, Yb and Lu can be used. Lanthanum alkoxide or Samarium alkoxide, which is industrially readily available, is preferably used.

The lanthanoid metal alkoxide of the present invention include multimers in addition to monomers depending on the kind of metal species and alkyl groups, and these multimers can also be used in the present invention.

Examples of the lanthanoid metal alkoxide include a compound of the formula (4):

$$Ln(OR^8)(OR^9)(OR^{10}) \qquad (4)$$

wherein, Ln represents a lanthanoid metal element, $R^8$, $R^9$ and $R^{10}$ are the same or different and independently represent an alkyl group having 1 to 10 carbon atoms.

The alkyl group having 1 to 10 carbon atoms for $R^8$, $R^9$ and $R^{10}$ may independently represent a straight, branched or cyclic alkyl group, and may bond together at their terminals to form a divalent or trivalent alkoxide residue.

Examples thereof include methyl, ethyl, n-propyl, i-propyl, n-butyl, i-butyl, tert-butyl, n-pentyl, n-hexyl, n-octyl, n-nonyl, n-decyl, cyclopropyl, cyclobutyl, cyclopentyl, cyclohexyl and the like.

As the alkoxide group, methoxide, ethoxide, n-propoxide, i-propoxide, butoxide and the like are preferred since preparation thereof is easy n-Propoxide, i-propoxide and butoxide are more preferred because of solubility, and i-propoxide is most preferred because of preparation cost, advantageous production operation, and the like.

These lanthanoid metal alkoxide can be obtained by known preparation methods.

The wonohydroxy compound (2) can be allowed to react with the above-described lanthanoid metal alkoxide and then the resulting can be used in reacting the cyclopropanecarboxylate of the formula (1) with the monohydroxy compound (2).

An amount of a lanthanoid metal alkoxide is not particularly restricted but may be catalytic, and is usually in the range of 0.001 to 200 mol %, preferably 0.1 to 10 mol % based on cyclopropanecarboxylate (1).

In the cyclopropanecarboxylate of the formula (1), $R^1$, $R^2$, $R^3$, $R^4$ and $R^5$ each independently represent a hydrogen atom, halogen atom, an optionally substituted alkyl group, an optionally substituted alkenyl group, an optionally substituted aralkyl or an optionally substituted aryl group.

The optionally substituted alkyl group includes, for example, an optionally substituted straight, branched or cyclic alkyl groups having 1 to 10 carbon atoms, which may be optionally substituted with a member selected from a halogen atom (e.g., fluorine, chlorine, bromine, iodoine), a (C1–C3)alkoxy group, a (C1–C5)alkoxylcarbonyl group, a (C1–C5)alkylsulfonyl group and a hydroxyimino group of which hydrogen atom in the hydroxy group may be replaced by a member selected from a phenyl group, a (C1–C3)alkyl group, a (C3–C6)alkenyl group and a (C3–C6)alkynyl group.

Specific examples thereof include methyl, ethyl, n-propyl, i-propyl, n-butyl, sec-butyl, tert-butyl, n-pentyl, n-hexyl, cyclohexyl, menthyl, chloromethyl, dichloromethyl, trichloromethyl, bromomethyl, dibromomethyl, tribromomethyl, 1-chloroethyl, 2-chloroethyl, 1-bromoethyl, 2-bromoethyl, 1,2-dichloroethyl, 1,2-dibromoethyl, 2,2,2-trichloroethyl, 2,2,2-tribromoethyl, methoxymethyl, 2-methoxyethyl, phenoxyiminomethyl, methoxyiminomethyl, allyoxyiminomethyl, propargyloxyiminomethyl, hydroxyiminomethyl and the like.

The optionally substituted alkenyl group include a (C2–C5)alkenyl group optionally substituted by a member selected from a halogen atom, a phenyl group, a halo-substituted (C2–C4)alkylene group, a (C1–C5) alkoxycarbonyl group, a (C1–C5)alkylsulfonyl group, a (C1–C3)alkylsulfonyloxy group and a hydroxyimino group of which hydrogen atom in the hydroxy group may be replaced by a member selected from a phenyl group, a (C1–C3)alkyl group, a (C3–C6)alkenyl group and a (C3–C6)alkynyl group.

Specific examples thereof include vinyl, 1-methylvinyl, 1-propenyl, 2-methyl-1-propenyl, 2,2-dichlorovinyl, 2,2-dibromovinyl, 2-chloro-2-fluorovinyl, 2-chloro-2-trifluoromethylvinyl, 2-bromo-2-tribromomethylvinyl and the like.

The optionally substituted aralkyl group include a phenyl- or naphthyl-substituted (C1–C2)alkyl group which may be optionally substituted by a member selected from (C1–C10) alkyl group and a (C1–C6)alkoxy group (e.g., methoxy, ethoxy, n-propoxy, i-propoxy, n-butoxy, sec-butoxy, t-butoxy, cyclohexloxy and the like) or a halogen atom and the like on the phenyl or naphthyl ring.

Specific examples thereof include benzyl, diphenylmethyl, phenylethyl, naphthylmethyl, naphthylethyl and the like The optionally substituted aryl group include a phenyl or naphthyl group which may be optionally substituted with the above-described (C1–C10)alkyl group and/or a (C1–C10) alkoxy group or halogen atom and the like on the phenyl or naphthyl ring.

Specific examples thereof include phenyl, 1-naphthyl, 2-naphthyl and the like.

In the formula (1), $R^6$ represents an alkyl group having 1 to 10 carbon atoms or an optionally substituted phenyl group.

The alkyl group having 1 to 10 carbon atoms may be straight, branched or cyclic, and specific examples thereof include methyl, ethyl, n-propyl, i-propyl, n-butyl, sec-butyl, tert-butyl, n-pentyl, n-hexyl, cyclohexyl, menthyl and the like. Methyl and ethyl are preferred.

The phenyl group may be optionally substituted by a group selected from (C1–C10)alkyl group and (C1–C10) alkoxy group or a halogen atom and the like.

Specific examples of the cyclopropanecarboxylate (1) include methyl cyclopropanecarboxylate, methyl 2-fluorocyclopropanecarboxylate, methyl 2,2-dichlorocyclopropanecarboxylate, methyl 2,2,3,3-tetramethylcyclopropanecarboxylate, methyl 2,2-dimethyl-3-(1-propenyl)cyclopropanecarboxylate, methyl 2,2-dimethyl-3-(2-methyl-1-propenyl) cyclopropanecarboxylate, methyl 2,2-dimethyl-3-(3-methyl-2-butenyl)cyclopropanecarboxylate, methyl 2,2-dimethyl-3-(2,2-dichlorovinyl)cyclopropanecarboxylate, methyl 2,2-dimethyl-3-(2,2,2-trichloroethyl) cyclopropanecarboxylate, methyl 2,2-dimethyl-3-(2-chloro-2-fluorovinyl)cyclopropanecarboxylate, methyl 2,2-dimethyl-3-(2-bromovinyl)cyclopropanecarboxylate, methyl 2,2-dimethyl-3-(2,2-dibromovinyl) cyclopropanecarboxylate, methyl 2,2-dimethyl-3-(1,2,2,2-tetrabromoethyl)cyclopropanecarboxylate, methyl 2,2-dimethyl-3-(1,2-dibromo-2,2-dichloroethyl)-cyclopropanecarboxylate, methyl 2,2-dimethyl-3-(2-chloro-3,3,3-trifluoro-1-propenyl)cyclopropanecarboxylate, methyl 2,2-dimethyl-3-[3,3,3-trifluoro-2-(trifluoromethyl)-1-propenyl]-cyclopropanecarboxylate, methyl 2,2-dimethyl-3-(2-phenyl-1-propenyl)cyclopropanecarboxylate, methyl 2,2-dimethyl-3-(2-phenylvinyl)cyclopropanecarboxylate, methyl 2,2-dimethyl-3-(2-methyl-3-phenyl-2-butenyl) cyclopropanecarboxylate, methyl 2,2-dimethyl-3-[(2,2-difluorocyclopropyliden)-methyl]cyclopropanecarboxylate, methyl 2,2-dimethyl-3-[2-(tert-butoxtcarbonyl)-vinyl] cyclopropanecarboxylate, methyl 2,2-dimethyl-3-[2-fluoro-2-(methoxycarbonyl)-vinyl]cyclopropanecarboxylate, methyl 2,2-dimethyl-3-[2-fluoro-2-(ethoxycarbonyl)-vinyl] cyclopropanecarboxylate, methyl 2,2-dimethyl-3-[2-fluoro-2-(tert-butoxycarbonyl)-vinyl]cyclopropanecarboxylate, methyl 2,2-dimethyl-3-[2-[2,2,2-trifluoro-1-(trifluoromethyl)ethoxycarbonyl]vinyl]-cyclopropanecarboxylate, methyl 2,2-dimethyl-3-(4-aza-4-methoxy-3-methylbuta-1,3-dienyl) cyclopropanecarboxylate, methyl 2,2-dimethyl-3-[2-[(tert-butyl)sulfonyl]-2-(tert-butoxycarbonyl)vinyl] cyclopropanecarboxylate, methyl 2,2-dimethyl-3-[2,2-dibromo-2-(hydroxysulfinyl)-1-(methoxy)ethyl] cyclopropanecarboxylate, methyl 2,2-dimethyl-3-(methylsulfonyl)-3-[2-(tert-butylsulfonyl)-2-(tert-butoxycarbonyl)ethyl]-cyclopropanecarboxylate, methyl 2,2-dimethyl-3-[2,2,2-tribromo-1-(methylsulfonyloxy) ethyl]cyclopropanecarboxylate, methyl 2-methyl-2-ethyl-3-(1-propenyl)cyclopropanecarboxylate, methyl 2,2-diethyl-3-(2,2-dichlorovinyl)cyclopropanecarboxylate, methyl 2-methyl-2-phenyl-3-(2-methyl-1-propenyl)-cyclopropanecarboxylate, methyl 2,2-dimethyl-3-(methoxyiminomethyl)cyclopropanecarboxylate, methyl 2,2-dimethyl-3-(phenoxyiminomethyl) cyclopropanecarboxylate, methyl 2,2-dimethyl-3-(allyloxyiminomethyl)cyclopropanecarboxylate, methyl 2,2-dimethyl-3-(propargyloxyiminomethyl)-cyclopropanecarboxylate, methyl 2,2-dimethyl-3-(hydroxyiminomethyl)cyclopropanecarboxylate, and cyclopropanecarboxylic acid esters in which the methyl group in the above described compounds are replaced by an ethyl group, a butyl group or a menthyl group.

Among these compounds esters such as 2,2-dimethyl-3-(2,2-dichlorovinyl)cyclopropanecarboxylate, 2,2-dimethyl-3-(2-methyl-1-propenyl)cyclopropanecarboxylate and 2,2-dimethyl-3-(methoxyiminomethyl) cyclopropanecarboxylate are preferred.

$R^7$ in the monohydroxy compound of the formula (2) used in the present invention will be explained below.

The optionally substituted alkyl group include:
a (C1–C10)alkyl group which may be optionally substituted by a group selected from:
a halogen atom,
a (C3–C4)alkenyl group which maybe substituted with a halogen atom,
a (C3–C4)alkynyl group,
a (C5–C6)cycloalkyl group,
a (C5–C6)cycloalkenyl group,
a heterocyclic group selected from:
a furyl group which may be substituted with a phenoxy group, a benzyl group, difluoromethyl group or a propynyl group, a pyrrolyl group substituted with a propynyl group andoptionally witha halomethyl group, a thiazolyl group substituted with a halomethyl group or a halomethoxy group, an isoxazolyl group optionally substituted by a methyl group, a 4,5,6,7-tetrahydroisoindol-1,3-dione-2-yl group, a 1-propynyl-imidazolidine-2,4-dione-3-yl group, a pyrazolyl group substituted with a propyne group and a halomethyl group, a halo-pyridyl group, and a thiazolin-2-one-5-yl group substituted with a methyl group and a propynyl group;

a (C5–C6)oxocycloalkenyl group substitutedby a methyl group and either a propenyl group or a propynyl group.

The optionally substituted aralkyl group include:

an optionally substituted (C6–C18)aralkyl group such as a phenyl-, naphthyl-, or anthracenyl-substituted (C1–C4)alkyl group, which phenyl-, naphthyl-, or anthracenyl group may be optionally substituted by a group selected from:

a nitro group, a cyano group, a halogen atom, a (C1–C10) alkyl group, a (C1–C3)haloalkly group, a (C1–C3) alkoxy group, a (C1–C3)haloalkoxy group, a (C1–C3) alkoxy(C1–C3)alkyl group, an amino group, a (C3–C5) alkynyl group, a haloacetyloxy(C1–C3)alkyl group, a thienyl group, a phenyl group, and a phenoxy group which may be substituted with a halogen atom, and said (C1–C4)alkyl group maybe substituted with a cyano group or form a indanyl group with the phenyl group.

The optionally substituted aryl group include:

a phenyl or naphthyl group which may be optionally substituted by a group selected from a halogen atom, a (C1–C10)alkyl group, a (C1–C10)alkoxy group, a (C3–C5)alkynyl group, an acetyl group and an aldehyde group.

The monohydroxy compound of the formula (2) used in the present invention include alkyl alcohol, aralkyl alcohol, aryl alcohol, all of which may be optionally substituted.

Examples of the optionally substituted alkyl alcohol include:

a (C1–C10)alkyl alcohol compound such as methyl alcohol, ethyl alcohol, n-propyl alcohol, i-propyl alcohol, n-butyl alcohol, sec-butyl alcohol, tert-butyl alcohol, n-pentyl alcohol, neopentyl alcohol, amyl alcohol, n-hexyl alcohol, n-octyl alcohol and n-decyl alcohol;

a (C1–C10)alkyl alcohol substituted with a heterocyclic group as defined above such as 2-furylmethyl alcohol, 3-furylmethyl alcohol, (5-phenoxy-3-furyl)methyl alcohol, (5-benzyl-3-furyl)methane-1-ol, [5-(difluoromethyl)-3-furyl]methane-1-ol, 5-propargyl-2-furfuryl alcohol, (5-methylisoxazol-3-yl)methane-1-ol, 1-[2-(trifluoromethyl)-1,3-thiazol-4-yl]prop-2-yn-1-ol, 1-[2-(trifluoromethoxy)-1,3-thiazol-4-yl]prop-2-yn-1-ol, 1-[1-prop-2-ynyl-5-(trifluoromethyl)pyrrol-3-yl] prop-2-yn-1-ol, (1-prop-2-ynylpryrrol-3-yl)methan-1-ol, 3-(hydroxymethyl)-1-propynyl-imidazolydine-2,4-dione, 2-(hydroxymethyl)-4,5,6,7-tetrahydroisoindole-1,3-dione, [1-(2-propynyl)pyrrol-3-yl]methan-1-ol, 5-(hydroxymethyl)-4-methyl-(2-propynyl)-1,3-thiazolin-2-one, [1-(2-propynyl)-5-(trifluoromethyl)-4-pyrazolyl]methan-1-ol, (1-prop-2-ynyl-2-methylindol-3-yl)methane-1-ol, [1-prop-2-ynyl-2-(trifluormethyl) indol-3-yl]methan-1-ol, or (2,3,6-trifluoro-4-pyridyl) methane-1-ol;

a (C1–C10)alkyl group which may be optionally substituted by a halogen atom such as fluoroethyl alcohol, trifluoroethyl alcohol, 3,3-dibromo-2-propen-1-ol, hexafluoroisopropyl alcohol, perfluorobutyl alcohol, perfluoropentyl alcohol, perfluorohexyl alcohol, perfluorooctyl alcohol, perfluorodecyl alcohol;

a (C1–C10)alkyl group which may be substituted with a (C3–C4)alkenyl group which may be substituted with a halogen atom and a (C3–C4)alkynyl group such as 4-fluorohept-4-en-1-yn-3-ol, or 4-methylhept-4-en-1-yn-3-ol; and a (C5–C6)oxocycloalkenyl group substituted with a methyl group and either a propenyl group or a propynyl group such as 4-hydroxy-3-methyl-2-(2-propenyl)-2-cyclopentene-1-one, or 4-hydroxy-3-methyl-2-(2-propinyl)-2-cyclopentene-1-one.

Examples of the optionally substituted aralkyl group include: benzyl alcohol, 2-methyl-3-phenylbenzyl alcohol, 2,3,5,6-tetrafluorobenzyl alcohol, 6-chloro-2,3,4-trifluorobenzyl alcohol, 2-chloro-3,6-difluorobenzyl alcohol, 4-(trifluoromethyl)benzyl alcohol, 2,3,4,5-tetrafluoro-6-methylbenzyl alcohol, 3-phenylbenzyl alcohol, 2,6-dichlorobenzyl alcohol, 3-phenoxybenzyl alcohol, 2-hydroxy-2-(3-phenoxyphenyl)ethanenitrile, 2-hydroxy-2-[4-(methoxymethyl)phenyl]ethanenitrile, 2-[3-(4-chlorophenoxy)phenyl]-2-hydroxyethanenitrile, 2-(4-amino-2,3,5,6-tetrafluorophenyl)-2-hydroxyethanenitrile, 2-(4-fluoro-3-phenoxyphenyl)-2-hydroxyethanenitrile, (2-methylphenyl)methyl alcohol, (3-methylphenyl)methyl alcohol, (4-methylphenyl)methyl alcohol, (2,3-dimethylphenyl)methyl alcohol, (2,4-dimethylphenyl) methyl alcohol, (2,5-dimethylphenyl)methyl alcohol, (2,6-dimethylphenyl)methyl alcohol, (3,4-dimethylphenyl) methyl alcohol, (2,3,4-trimethylphenyl)methyl alcohol, (2,3,5-trimethylphenyl)methyl alcohol, (2,3,6-trimethylphenyl)methyl alcohol, (3,4,5-trimethylphenyl)methyl alcohol, (2,4,6-trimethylphenyl)methyl alcohol, (2,3,4,5-tetramethylphenyl)methyl alcohol, (2,3,4,6-tetramehylphenyl)methyl alcohol, (2,3,5,6-tetramethylphenyl)methyl alcohol, (pentamethyphenyl) methyl alcohol, (ethylphenyl)methyl alcohol, (n-propylphenyl )methyl alcohol, (i-propylphenyl)methyl alcohol, (n-butylphenyl)methyl alcohol, (sec-butylphenyl) methyl alcohol, (tert-butylphenyl)methyl alcohol, (n-pentylphenyl)methyl alcohol, (neopentylphenyl)methyl aldohol, (n-hexylphenyl)methyl alcohol, (n-octylphenyl) methyl alcohol, (n-decylphenyl)methyl alcohol, (n-dodecylphenyl)methyl alcohol, (n-tetradecylphenyl) methyl alcohol, naphthylmethyl alcohol, anthracenylmethyl alcohol, 1-phenylethyl alcohol, 1-(1-naphthyl)ethyl alcohol, 1-(2-naphtyl)ethyl alcohol, (4-prop-2-ynylphenyl)methane-1-ol, (3-prop-2-ynylphenyl)methane-1-ol, 4-prop-2-enylindane-1-ol, 4-phenylindane-2-ol, 4-(2-thienyl)indane-2-ol.

Examples of the optionally substituted aryl alcohol include phenol, 1-naphthol, 2-naphthol, 4-prop-2-ynylphenol, 3-prop-2-ynylphenol, 4-hydroxyacetophenone, 4-hydroxybenzaldehyde and the like, and compounds obtained by substitution with a (C1–C10)alkyl group, a (C1–C10)alkoxy group or halogen atom and the like on the aromatic ring.

Among the alcohol compound of the formula (2), a primary alcohol is preferred and more preferred is an alcohol wherein $R^7$ group is an optionally substituted phenylmethyl group, which phenyl group may be optionally substituted by a group selected from:

a nitro group, a cyano group, a halogen atom, a (C1–C10) alkyl group, a (C1–C3)haloalkly group, a (C1–C3) alkoxy group, a (C1–C3)haloalkoxy group, a (C1–C3) alkoxy(C1–C3)alkyl group, an amino group, a (C3–C5) alkynyl group, a haloacetyloxy(C1–C3)alkyl group, a thienyl group, a phenyl group, and a phenoxy group which may be substituted with a halogen atom.

More specifically, 3-phenoxybenzyl alcohol is preferred.

An amount of the monohydroxy compound (2) is usually one mole or more per mole of cyclopropanecarboxylate (1), and also it may be used in excess amount or can be used as a solvent. Unreacted monohydroxy compound (2) can be recovered by, for example, an operation such as distillation and the like after termination of the reaction.

The reaction of cyclopropanecarboxylate (1) with a monohydroxy compound (2) in the presence of a lanthanoid metal alkoxide is usually carried out under an inert gas atmosphere such as argon, nitrogen and the like.

The reaction may be carried out at atomospheric pressure, increased pressure or reduced pressure, preferably at atmospheric pressure or reduced pressure.

The reaction is preferably conducted while removing an alcohol derived from cyclopropanecarboxylate (1) out of the reaction system continuously by a method such as distillation and the like when the resulting alcohol has a lower boiling point.

The reaction can be carried out without solvent or in an inert solvent, and examples of the solvent include halogenated hydrocarbons such as dichloromethane, chloroform, 1,2-dichloroethane and the like, aliphatic hydrocarbons such as hexane, heptane, octane, nonane and the like, aromatic hydrocarbons such as benzene, toluene, xylene, chlorobenzene and the like, ether solvents such as diethyl ether, tetrahydrofuran, and the like.

An alcohol derived from cyclopropanecarboxylate (1) may be continuously removed by adding a solvent that forms an azeotrope with the alcohol.

The reaction temperature is not particularly restricted, and is usually in the range of 20 to 200° C.

The alkoxide of the lanthanoid metal can be removed from cyclopropanecarboxylates (3) produced, for example, by extraction, washing with water or acidic water, and the like, and the desired product can be readily separated from the reaction mixture by a conventional operation such as evaporation, and may be further purified by distillation and the like, if necessary.

The present invention can provide cyclopropanecarboxylates (3) readily in good yield, and it is advantageous as an industrial production method thereof.

EXAMPLES

The following examples further illustrate the present invention in more detail, but do not limit the scope of the invention.

Example 1

Into a schlenk-type tube purged with nitrogen were added 0.13 g (0.4 mmol) of triisopropoxysamarium (III), 1.78 g (8 mmol) of methyl 2,2-dimethyl-3-(2,2-dichlorovinyl)cyclopropanecarboxylate and 3.39 g (16 mmol) of 3-phenoxybenzyl alcohol, then, the mixture was stirred for 1.5 hours at 90° C. When the reaction mixture was analyzed by gas chromatography, the yield of (3-phenoxyphenyl)methyl 2,2-dimethyl-3-(2,2-dichlorovinyl)cyclopropanecarboxylate was 99%.

Example 2

Into a schlenk-type tube purged with nitrogen were added 0.13 g (0.4 mmol) of triisopropoxylanthanum (III), 1.75 g (8 mmol) of methyl 2,2-dimethyl-3-(2,2-dichlorovinyl)cyclopropanecarboxylate and 3.27 g (16 mmol) of 3-phenoxybenzyl alcohol, then, the mixture was stirred for 1.5 hours at 90° C. When the reaction mixture was analyzed by gas chromatography, the yield of (3-phenoxyphenyl)methyl 2,2-dimethyl-3-(2,2-dichlorovinyl)cyclopropanecarboxylate was 94%.

Example 3

Into a schlenk-type tube purged with nitrogen were added 0.19 g (0.6 mmol) of triisopropoxysamarium (III), 2.87 g (12.8 mmol) of methyl 2,2-dimethyl-3-(2,2-dichlorovinyl)cyclopropanecarboxylate and 2.56 g (12.8 mmol) of 3-phenoxybenzyl alcohol, then, the mixture was stirred for 6 hours at 90° C. When the reaction mixture was analyzed by gas chromatography, the yield of (3-phenoxyphenyl)methyl 2,2-dimethyl-3-(2,2-dichlorovinyl)cyclopropanecarboxylate was 93%.

Example 4

Into a schlenk-type tube purged with nitrogen were added 0.16 g (0.5 mmol) of triisopropoxysamarium (III), 1.96 g (10.0 mmol) of ethyl 2,2-dimethyl-3-(2-methyl-1-propenyl)cyclopropanecarboxylate and 4.00 g (20.0 mmol) of 3-phenoxybenzyl alcohol, then, the mixture was stirred for 12 hours at 130° C. When the reaction mixture was analyzed by gas chromatography, the yield of (3-phenoxyphenyl)methyl 2,2-dimethyl-3-(2,2-dichlorovinyl)cyclopropanecarboxylate was 92%.

Example 5

Into a schlenk-type tube purged with nitrogen tube were added 0.16 g (0.5 mmol) oftriisopropoxylanthanum (III), 1.96 g (10.0 mmol) of ethyl 2,2-dimethyl-3-(2-methyl-1-propenyl)cyclopropanecarboxylate and 4.00 g (20.0 mmol) of 3-phenoxybenzyl alcohol, then, the mixture was stirred for 12 hours at 130° C. When the reaction mixture was analyzed by gas chromatography, the yield of (3-phenoxyphenyl)methyl 2,2-dimethyl-3-(2,2-dichlorovinyl)cyclopropanecarboxylate was 90%.

Comparative Example 1

Into a schlenk-type tube purged with nitrogen were added 0.13 g (0.4 mmol) of tetraisopropoxytitanium (IV), 1.75 g (8 mmol) of methyl 2,2-dimethyl-3-(2,2-dichlorovinyl)cyclopropanecarboxylate and 3.27 g (16 mmol) of 3-phenoxybenzyl alcohol, then, the mixture was stirred for 3 hours at 90° C. When the reaction mixture was analyzed by gas chromatography, the yield of (3-phenoxyphenyl)methyl 2,2-dimethyl-3-(2,2-dichlorovinyl)cyclopropanecarboxylate was 31%.

Comparative Example 2

Into a schlenk-type tube purged with nitrogen tube were added 0.11 g (0.4 mmol) of anhydrous samarium chloride (III), 1.86 g (8.3 mmol) of methyl 2,2-dimethyl-3-(2,2-dichlorovinyl)cyclopropanecarboxylate and 3.45 g (17.2 mmol) of 3-phenoxybenzyl alcohol, then, the mixture was stirred for 5 hours at 90° C. When the reaction mixture was analyzed by gas chromatography, the yield of (3-phenoxyphenyl)methyl 2,2-dimethyl-3-(2,2-dichlorovinyl)cyclopropanecarboxylate was 5%.

Example 6

Into a schlenk-type tube purged with nitrogen were added 0.16 g (0.5 mmol) of triisopropoxylanthanum (III), 2.23 g (10.0 mmol) of ethyl 2,2-dimethyl-3-(2,2-dichlorovinyl)cyclopropancarboxylate, 2.40 g (12.0 mmol) of 3-phenoxybenzyl alcohol and 5.5 g of heptane, then, the mixture was stirred for 12 hours under reflux. The yield of (3-phenoxyphenyl)methyl 2,2-dimethyl-3-(2,2-dichlorovinyl)cyclopropanecarboxylate was 96% based on Gas chromatography analysis of the reaction mixture.

Example 7

Into a schlenk-type tube purged with nitrogen were added 0.16 g (0.5 mmol) oftriisopropoxylanthanum (III), 2.23 g (10.0 mmol) of ethyl 2,2-dimethyl-3-(2,2-dichlorovinyl)cyclopropancarboxylate, 2.00 g (10.0 mmol) of 3-phenoxybenzyl alcohol and 5.5 g of heptane, then, the mixture was stirred for 8 hours under reflux. The yield of (3-phenoxyphenyl)methyl 2,2-dimethyl-3-(2,2-dichlorovinyl)cyclopropanecarboxylate was 92% based on Gas chromatography analysis of the reaction mixture.

Example 8

Into a schlenk-type tube purged with nitrogen were added 0.16 g (0.5 mmol) of triisopropoxylanthanum (III) and 2.20 g (11.0 mmol) of 3-phenoxybenzyl alcohol, the resulting mixture was stirred at 60° C. and 50 Torr, which corresponds to 66.6 hPa, for 2 hrs. Then 2.23 g (10.0 mmol) of ethyl 2,2-dimethyl-3-(2,2-dichlorovinyl)cyclopropancarboxylate, and 5.5 g of heptane were added thereto and the mixture was stirred for 15 hours under reflux. The yield of (3-phenoxyphenyl)methyl 2,2-dimethyl-3-(2,2-dichlorovinyl)cyclopropanecarboxylate was 99% based on Gas chromatography analysis of the reaction mixture.

Example 9

Into a schlenk-type tube purged with nitrogen were added 0.08 g (0.25 mmol) of triisopropoxylanthanum (III), 1.00 g (5.0 mmol) of vinyl 2,2-dimethyl-3-(2-methyl-1-propenyl)cyclopropanecarboxylate and 1.20 g (6.0 mmol) of 3-phenoxybenzyl alcohol, then, the mixture was stirred for 12 hours at 80° C. The yield of (3-phenoxyphenyl)methyl 2,2-dimethyl-3-(2-methyl-1-propenyl)cyclopropanecarboxylate was 97% based on Gas chromatography analysis of the reaction mixture.

Example 10

Into a schlenk-type tube purged with nitrogen were added 29 mg (0.09 mmol) of triisopropoxysamarium (III), 300 mg (1.78 mmol) of methyl 2,2-dimethyl-3-(1-propenyl)cyclopropanecarboxylate and 714 mg (3.56 mmol) of 3-phenoxybenzyl alcohol, then, the mixture was stirred for 8 hours at 110° C. The yield of (3-phenoxyphenyl)methyl 2,2-dimethyl-3-(1-propenyl)cyclopropanecarboxylate was 64% based on the Gas chromatography analysis of the reaction mixture.

Example 11

Into a 10 ml flask purged with nitrogen were added 35.4 mg (0.11 mmol) of triisopropoxysamarium (III), 200 mg (1.08 mmol) of methyl 2,2-dimethyl-3-(methoxyiminomethyl)cyclopropanecarboxylate and 432 mg (2.16 mmol) of 3-phenoxybenzyl alcohol, then the mixture was stirred for 8 hours at 110° C. The yield of (3-phenoxyphenyl)methyl 2,2-dimethyl-3-(methoxyiminomethyl)cyclopropanecarboxylate was 83%.

What is claimed is:

1. A method for producing cyclopropanecarboxylate of formula (3):

$$\begin{array}{c} R^3 \quad R^4 \\ R^1 \diagdown\!\!\!\!\bigtriangleup\!\!\!\!\diagup COOR^7 \\ R^2 \quad R^5 \end{array} \quad (3)$$

wherein $R^1$, $R^2$, $R^3$, $R^4$, and $R^5$ each independently represent:
  a hydrogen atom, a halogen atom,
  an optionally substituted alkyl group,
  an optionally substituted alkenyl group,
  an optionally substituted aralkyl group or
  an optionally substituted aryl group; and
$R^7$ represents:
  an optionally substituted alkyl group,
  an optionally substituted aralkyl group, or
  an optionally substituted aryl group,
which comprises:
  reacting a cyclopropanecarboxylate of formula (1)

$$\begin{array}{c} R^3 \quad R^4 \\ R^1 \diagdown\!\!\!\!\bigtriangleup\!\!\!\!\diagup COOR^6 \\ R^2 \quad R^5 \end{array} \quad (1)$$

wherein $R^1$, $R^2$, $R^3$, $R^4$, and $R^5$ are as defined above, and
$R^6$ represents an alkyl group having 1 to 10 carbon atoms, a vinyl group, or an optionally substituted phenyl group,
with a monohydroxy compound of formula (2):

$$R^7OH \quad (2)$$

wherein $R^7$ is the same as defined above,
in the presence of a samarium alkoxide, and
provided that $R^6$ and $R^7$ are different.

2. The method according to claim 1, wherein $R^1$, $R^2$, $R^3$, $R^4$, and $R^5$ each independently represent:
  an optionally substituted straight, branched or cyclic alkyl group having 1 to 10 carbon atoms, which alkyl group may be optionally substituted with a member selected from:
    a halogen atom, a (C1–C3) alkoxy group, a (C1–C5) alkoxylcarbonyl group, a (C1–C5) alkylsulfonyl group and a hydroxyimino group of which hydrogen atom in the hydroxy group may be replaced by a member selected from a phenyl group, a (C1–C3) alkyl group, a (C3–C6) alkenyl group and a (C3–C6) alkynyl group,
  a (C2–C5) alkenyl group optionally substituted by a member selected from a halogen atom, a phenyl group, a halo-substituted (C2–C4) alkylene group, a (C1–C5) alkoxycarbonyl group, a (C1–C5) alkylsulfonyl group, a (C1–C3) alkylsulfonyloxy group and a hydroxyimino group of which hydrogen atom in the hydroxy group may be replaced by a member selected from a phenyl group, a (C1–C3) alkyl group, a (C3–C6) alkenyl group and a (C3–C6) alkynyl group,
  a phenyl- or naphthyl-substituted (C1–C2) alkyl group which may be optionally substituted by a member selected from a (C1–C10) alkyl group and a (C1–C6) alkoxy group, or a phenyl or naphthyl group which may be optionally substituted with a (C1–C10) alkyl group, a (C1–C10) alkoxy group or a halogen atom;

$R^6$ represents:

an alkyl group having 1 to 10 carbon atoms, a vinyl group, or a phenyl group that may be optionally substituted by a group selected from a (C1–C10) alkyl group and a (C1–C10) alkoxy group or a halogen atom;

$R^7$ represents:

a (C1–C10) alkyl group which may be optionally substituted by a group selected from:
  a halogen atom,
  a (C3–C4) alkenyl group which may be substituted with a halogen atom,
  a (C3–C4) alkynyl group,
  a (C5–C6) cycloalkyl group,
  a (C5–C6) cycloalkenyl group,
  a heterocyclic group selected from:
    a furyl group which may be substituted with a phenoxy group, a benzyl group, difluoromethyl group or a propynyl group,
    a pyrrolyl group substituted with a propynyl group and optionally with a halomethyl group,
    a thiazolyl group substituted with a halomethyl group or a halomethoxy group,
    an isoxazolyl group optionally substituted by a methyl group,
    a 4,5,6,7-tetrahydroisoindol-1,3-dione-2-yl group,
    a 1-propynyl-imidazolidine-2,4-dione-3-yl group,
    a pyrazolyl group substituted with a propynyl group and a halomethyl group,
    a halo-pyridyl group, and
    a thiazolin-2-one-5-yl group substituted with a methyl group and a propynyl group; or
a (C5–C6) oxocycloalkenyl group substituted with a methyl group and either a propynyl group or a propenyl group, and provided that $R^6$ and $R^7$ are different.

3. The method according to claim 1 or 2, wherein the lanthanoid metal is Sm.

4. The method according to claim 3, wherein the lanthanoid metal alkoxide is $Sm(OiPr)_3$.

5. The method according to claim 1, wherein $R^6$ in cyclopropanecarboxylate of the formula (1) represents methyl or ethyl.

6. The method according to claim 5, wherein the cyclopropanecarboxylate of the formula (1) represent 2,2-dimethyl-3-(2,2-dichlorovinyl)cyclopropanecarboxylate.

7. The method according to claim 5, wherein the cyclopropanecarboxylate of the formula (1) is 2,2-dimethyl-3-(2-methyl-1-propenyl)cyclopropanecarboxylate.

8. The method according to claim, 5, wherein the cyclopropanecarboxylate of the formula (1) is 2,2-dimethyl-3-(methoxyiminomethyl)cyclopropanecarboxylate.

9. The method according to claims 5, wherein the cyclopropanecarboxylates of the formula (1) is 2,2-dimethyl-3-(1-propenyl)cyclopropanecarboxylate.

10. The method according to claim 1, wherein the monohydroxy compound of the formula (2) is a primary alcohol.

11. The method according to claim 10, wherein $R^7$ represents an optionally substituted phenylmethyl group, which phenyl group may be optionally substituted by a group selected from:

a nitro group, a cyano group, a halogen atom, a (C1–C10) alkyl group, a (C1–C3)haloalkly group, a (C1–C3) alkoxy group, a (C1–C3)haloalkoxy group, a (C1–C3) alkoxy(C1–C3)alkyl group, an amino group, a (C3–C5) alkynyl group, a haloacetyloxy(C1–C3)alkyl group, a thienyl group, a phenyl group, and a phenoxy group which may be substituted with a halogen atom.

12. The method according to claim 11, wherein the monohydroxy compound of the formula (2) is 3-phenoxybenzyl alcohol.

* * * * *